(12) United States Patent
Dasgupta et al.

(10) Patent No.: US 9,354,170 B2
(45) Date of Patent: May 31, 2016

(54) NIR FLUORESCENCE OF HEAVY WATER

(75) Inventors: Anjan Kr. Dasgupta, Kolkata (IN); Hirak Kumar Patra, District West Midnapore (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 1045 days.

(21) Appl. No.: 13/376,102

(22) PCT Filed: Apr. 5, 2011

(86) PCT No.: PCT/IB2011/000733
§ 371 (c)(1),
(2), (4) Date: Dec. 2, 2011

(87) PCT Pub. No.: WO2012/110842
PCT Pub. Date: Aug. 23, 2012

(65) Prior Publication Data
US 2012/0206721 A1 Aug. 16, 2012

(30) Foreign Application Priority Data
Feb. 15, 2011 (IN) .............................. 196/KOL/2011

(51) Int. Cl.
*G01N 21/64* (2006.01)
(52) U.S. Cl.
CPC ........ *G01N 21/64* (2013.01); *G01N 2021/6421* (2013.01)
(58) Field of Classification Search
CPC .................................................... G01N 21/64
USPC ..................................................... 250/338.1
See application file for complete search history.

(56) References Cited

U.S. PATENT DOCUMENTS

| | | | |
|---|---|---|---|
| 7,255,835 B2 * | 8/2007 | Franzen et al. | 422/82.11 |
| 7,749,726 B2 | 7/2010 | Chuck | |
| 7,973,285 B2 * | 7/2011 | Han et al. | 250/339.1 |
| 2003/0187335 A1 | 10/2003 | McCarthy | |
| 2004/0001826 A1 | 1/2004 | Gill et al. | |
| 2006/0099146 A1 | 5/2006 | Chow et al. | |
| 2008/0076188 A1 | 3/2008 | Patsenker et al. | |

(Continued)

FOREIGN PATENT DOCUMENTS

| | | |
|---|---|---|
| IN | 1076/KOL/2009 | 4/2010 |
| WO | WO-2008/064408 | 6/2008 |

OTHER PUBLICATIONS

Bhagat, A. et al., "Continuous Particle Separation in Spiral Microchannels Using Dean Flows and Differential Migration," Lab on a Chip, 2008, vol. 8, pp. 1448-1453.

(Continued)

*Primary Examiner* — David Porta
*Assistant Examiner* — Faye Boosalis
(74) *Attorney, Agent, or Firm* — Foley & Lardner LLP

(57) ABSTRACT

A method includes detecting $D_2O$ in a sample by fluorescence spectroscopy. The fluorescence spectroscopy may be near-infrared fluorescence spectroscopy. The method may include observing an excitation wavelength of the sample at 620 nm to 640 nm. The method may also include observing an emission wavelength of the sample at 900 nm to 1000 nm. The method includes detecting $D_2O$ and $D_2O$ nano-clusters and their alterations in presence of suspended or colloidal objects including bio-molecules or cells, by emission spectroscopy.

20 Claims, 10 Drawing Sheets

(56) References Cited

U.S. PATENT DOCUMENTS

| | | |
|---|---|---|
| 2008/0138909 A1 | 6/2008 | Wheeler et al. |
| 2008/0241262 A1 | 10/2008 | Lee et al. |
| 2009/0047300 A1 | 2/2009 | Abulrob et al. |
| 2009/0142261 A1 | 6/2009 | Hsu et al. |
| 2009/0220432 A1 | 9/2009 | Artemov et al. |
| 2009/0234225 A1 | 9/2009 | Martin et al. |
| 2009/0306291 A1 | 12/2009 | Shimaoka et al. |
| 2010/0178710 A1 | 7/2010 | Hamon et al. |
| 2010/0291575 A1 | 11/2010 | Shamah et al. |

OTHER PUBLICATIONS

Final Office Action on U.S. Appl. No. 13/123,209 dated Nov. 21, 2012.

Non-Final Office Action for U.S. Appl. No. 12/628,721 dated Jan. 31, 2012.

Non-Final Office Action on U.S. Appl. 13/123,209, mailed Jun. 21, 2012.

Patra, et al., "Near Infrared Fluorescence of Water and Sensing the Size and Surface of Nanometerem of Micrometre Scale Objects with Aqueous Interface".

Shertukde, H., et al., "Superior and Advanced Bio-Instrumentation to Identify and Isolate Stem-Cell Lineages: Graft Mapper and Stem Cell Identifier," Connecticut's Stem Cell Research International Symposium, New Haven, C.T., 2009, accessed online at: http://www.allacademic.com/meta/p369315_index.html. on May 22, 2012, pp. 1-3.

Stewart, Carleton C.; et al., "Flow Cytometer in the Infrared: Inexpensive Modifications to a Commercial Instrument," Cytometry; Part A 67A, 2005, pp. 104-111.

Uchugonova, A. and König, K., "Two-photon autofluorescence and second-harmonic imaging of adult stem cells," J. Biomed. Opt., vol. 13, Issue 5, 2008.

Xie, C., et al., "Near-infrared Raman spectroscopy of single optically trapped biological cells," Opt. Lett., vol. 27, issue 4, pp. 249-251, 2002.

Altermatt, H.J. et al., "Heavy water delays growth of human carcinoma in nude mice," Cancer, Aug. 1, 1988, vol. 62, pp. 462-466.

Amiot et al., "Near-Infrared Fluorescent Materials for Sensing of Biological Targets," Sensors, May 8, 2008, vol. 8, No. 5, pp. 3082-3105.

BD Biosciences, "BD FACSCalibur Flow Cytometer—The Automated, Multicolor Flow Cytometry System," Jun. 2002, retrieved on Dec. 14, 2010, http://www.mmcri.org/facility/pdf%20files/facs/FACScalibur.pdf, 11 pages.

Benson et al., "Fluorescence Properties of Indocyanine Green as Related to Angiography", Physics in Medicine and Biology, 1978, vol. 23, No. 1, pp. 159-163.

Berger, M. et al., "Design of a Microfabricated Magnetic Cell Separator," Electrophoresis, 2001, vol. 22, pp. 3883-3892.

Bertoncini, P. et al., Morphology of DNA/Single Walled Nanotubes Complexes, Digest Journal of Nanomaterials and Biostructures, Dec. 2007, vol. 2, No. 4, pp. 293-297.

Bhagat, A. et al., "Continuous Particle Separation in Spiral Microchannels Using Dean Flows and Differential Migration," Lab on a Chip, 2008, vol. 8, pp. 1906-1914.

Bieback, K. et al., "Critical Parameters for the Isolation of Mesenchymal Stem Cells from Umbilical Cord Blood," Stem Cells, 2004, vol. 22, pp. 625-634.

Bonner, W. et al., "Fluorescence Activated Cell Sorting," The Review of Scientific Instruments, Mar. 1972, vol. 43, No. 3, pp. 404-409.

Chan, J.W. et al., "Label-free biochemical characterization of stem cells using vibrational spectroscopy," J. Biophoton., Aug. 5, 2009, vol. 2, No. 11, pp. 656-668.

Chan, J.W. et al., "Label-free separation of human embryonic stem cells (hESCs) and their cardiac derivatives using Raman Spectroscopy", Analytical Chemistry, Feb. 15, 2009, vol. 81, pp. 1324-1331 (1-17).

Chang, S. et al., "A Continuous Size-Dependent Particle Separator Using a Negative Dielectriphoretic Virtual Pillar Array," Lab on a Chip, 2008, vol. 8, pp. 1930-1936.

Cheng et al., "Near-Infrared Fluorescent RGD Peptides for Optical Imaging of Integrin αvβ3 Expression in Living Mice," Bioconjugate Chemistry, Oct. 29, 2005, vol. 16, No. 6, pp. 1433-1441.

Choi, S. et al., "Continuous Hydrophoretic Separation and Sizing of Microparticles Using Slanted Obstacles in a Microchannel," Lab on a Chip, 2007, vol. 7, pp. 890-897.

Dako, "Flow Cytometry Educational Guide 2nd Edition," 2006, retrieved on Dec. 14, 2010, http://harvardstemcellinstitute.org/CRM_Flow/documents/DAKO_flow_cytometry_educational_guide.pdf, 68 pages.

Douglas, C. et al., "Isolation of Pure Villous Cytotrophoblast from Term Human Placenta using Immonomagnetic Microspheres," Journal of Immunological Methods, 1989, vol. 119, pp. 259-268.

European Pharmacopoeia 5th Ed. Main vol. 5.0, 2.2.40., "Near-Infrared Spectrophotometry," Jul. 2004, pp. 59-63.

Frangioni, J.V., "In Vivo Near-Infrared Fluorescence Imaging", Current Opinion in Chemical Biology, Oct. 2003, vol. 7, pp. 626-634.

Frens, G., "Controlled nucleation for the regulation of the particle size in monodisperse gold suspensions," Nature Physical Science, Jan. 1, 1973, vol. 241, pp. 20-22.

Fu, A.Y. et al., "A Microfabricated Fluorescence-Activated Cell Sorter," Natural Biotechnology, Nov. 1999, vol. 17, pp. 1109-1111.

Gaeng, D.P. et al., "Paradoxical effects of bleomycin and heavy water (D2O) in mice," Int. J. Cancer, 1995, vol. 62, pp. 784-790.

Galanzha, E. et al., "In Vivo, Non-invasive, Label-Free Detection and Eradication of Circulating Metastatic Melanoma Cells using Two-Color Photoacoustic Flow Cytometry with a Diode Laser," Cancer Research, Oct. 15, 2009, vol. 69, No. 20, pp. 7926-7934 (1-17).

Gao et al., "In Vivo Cancer Targeting and Imaging with Semiconductor Quantum Dots", Nature Biotechnology, Aug. 2004, vol. 22, No. 8, pp. 969-976, Supplementary info 5 pages.

Gottlieb, H.E. et al., "NMR Chemical Shifts of Common Laboratory Solvents as Trace Impurities," J. Org. Chem., 1997, vol. 62, No. 21, pp. 7512-7515.

Han, K. et al., "Paramagnetic Capture Mode Magentophoretic Microseparator for High Efficiency Blood Cell Separations," Lab on a Chip, 2006, vol. 6, pp. 265-273.

Hanlon et al., "Near-Infrared Fluorescence Spectroscopy Detects Alzheimer's Disease in Vitro," Photochemistry and Photobiology, May 7, 1999, vol. 70, No. 2, pp. 236-242.

Hilger, I. et al., "Near-infrared fluorescence imaging of HER-2 protein over-expression in tumour cells," European Radiology, Apr. 30, 2004, vol. 14, pp. 1124-1129.

Hsu, C.-H. et al., "Microvortex for Focusing, Guiding and Sorting of Particles," Lab on a Chip, 2008, vol. 8, pp. 2128-2134.

Inglis, D. et al., "Microfluidic High Gradient Magnetic Cell Separation," Journal of Applied Physics, 2006, vol. 99, pp. 08k101-1-08k101-3.

Inokuchi, H. et al., "Development of Micro Immuno-Magnetic Cell Sorting System with Lamination Mixer and Magnetic Separator," Proceedings of 25th Sensor Symposium, 2008, pp. 851-852.

International Search Report and Written Opinion for PCT/IB2011/000733 mailed Jul. 14, 2011.

International Search Report and Written Opinion for PCT/IB2010/001954 mailed Dec. 16, 2010.

Jiang, Y. et al., "Pluripotency of Mesenchymal Stem Cells derived from Adult Marrow," Nature, advance online publication Jun. 20, 2002, pp. 1-9.

Jinendra, B. et al., "Near infrared spectroscopy and aquaphotomics: Novel approach for rapid in vivo diagnosis of virus infected soybean," Biochemical and Biophysical Research Communications, 2010, vol. 397, pp. 685-690.

Keller et al., "Evaluation of Brain Toxicity Following Near Infrared Light Exposure after Indocyanine Green Dye Injection", Journal of Neuroscience Methods, May 30, 2002, vol. 117, pp. 23-31.

Kim, Y. et al., "Determination of the Equilibrium Constant of the Isotropic Disproportionation Between Water and Heavy Water Using Near-Infrared Spectroscopy," Applied Spectroscopy, 2009, vol. 63, No. 2, 4 pages.

(56) References Cited

OTHER PUBLICATIONS

Krause, D. et al., "Multi-Organ, Multi-Lineage Engraftment by a Single Bone Marrow-Derived Stem Cell," Cell, May 4, 2001, vol. 105, pp. 369-377.
Lebedkin, S. et al. "Near-Infrared Photoluminescence of Single-Walled Carbon Nanotubes Prepared by the Laser Vaporization Method" AIP Conference Proceedings, Molecular Nanostructures: XVII International Winterschool Euroconference on Electronic Properties of Novel Materials, Oct. 20, 2003, vol. 685, pp. 148-151.
Lee, O. et al., "Isolation of Multipotent Mesenchymal Stem Cells from Umbilical Cord Blood," Blood, Mar. 1, 2004, vol. 103, No. 5, pp. 1669-1675.
Luck, W.A.P., "Near-infrared spectra of water and heavy water at temperatures between 25 and 390°," J. Phys. Chem., 1970, vol. 74, No. 22, pp. 4006-4007.
Markx, G. et al., "DEP-FFF: Field-Flow Fractionation Using Non-Uniform Electric Fields," Journal of Liquid Chromatography and Related Technologies, 1997, vol. 20, No. 16 & 17, pp. 2857-2872.
Michalet et al., "Quantum Dots for Live Cells", in Vivo Imaging, and Diagnostics, Science, Jan. 28, 2005, vol. 307, No. 5709, pp. 538-544 (1-16).
Miwa, J. et al., "Adhesion-Based Cell Sorter with Antibody-Coated Amino-Functionalized-Parylene Surface," Journal of Microelectro-Mechanical Systems, Jun. 2008, vol. 17, No. 3, pp. 611-622.
Morton, K. et al., "Crossing Microfluidic Streamlines to Lyse, Label and Wash Cells," Lab on a Chip, 2008, vol. 8, pp. 1448-1453.
Navea, S. et al.,"Modeling temperature-dependent protein structural transitions by combined near-IR and mid-IR spectroscopies and multivariate curve resolution," Anal. Chem., Oct. 15, 2003, vol. 75, No. 20, pp. 5592-5601.
Naftalin, R.J. et al., "3-O-methyl-D-glucose transport in rat red cells: effects of heavy water," Biochim. Biophys. Acta., 1991, vol. 1064, pp. 37-48.
Ohta, A. et al., "Dynamic Cell and Microparticle Control via Optoelectronic Tweezers," Journal of Microelectromechanical Systems, Jun. 2007, vol. 16, No. 3, pp. 491-499.
Pamme, N. et al., "On-Chip Free-Flow Magnetophoresis: Continuous Flow Separation of Magnetic Particles and Agglomerates", Analytical Chemistry, vol. 76, No. 24, Dec. 15, 2004, pp. 7250-7256.
Patra, H.K. et al., "Cell Selective Response to Gold Nanoparticles," Nanomedicine: Nanotechnology, Biology, and Medicine, 2007, vol. 3, pp. 111-119.
Pope, R.M. et al., "Absorption spectrum (380-700 nm) of pure water. II. Integrating cavity measurements," Applied Optics, Nov. 20, 1997, vol. 36, No. 33, pp. 8710-8723.
Rhyner et al., "Quantum Dots and Targeted Nanoparticle Probes for In Vivo Tumor Imaging", Fundamental Biomedical Technologies, Nanoparticles in Biomedical Imaging, 2008, vol. 102, Part 5, pp. 413-425.
Rosenthal, A. et al., "Dielectrophoretic Traps for Single-Particle Patterning," Biophysics Journal, Mar. 2005, vol. 88, pp. 2193-2205.
Saias, L. et al., "Microfluidic Magnetic Cell Sorting System for Cancer Diagnosis," Proceedings of 12th International Conference of Miniaturized Systems for Chemistry and Life Sciences (µTAS), Oct. 12-16, 2008, pp. 552-554.
Sailer, B.L. et al., "Differential effects of deuterium oxide on the fluorescence lifetimes and intensities of dyes with different modes of binding to DNA," J. Histochem. Cytochem.,1997, vol. 45, No. 2, pp. 165-175.
Sakudo, A. et al., "Near-infrared spectroscopy: Promising diagnostic tool for viral infections," Biochemical and Biophysical Research Communications, 2006, vol. 341, pp. 279-284.
Scolnik, Y. et al., "Subtle differences in structural transitions between poly-L- and poly-D-amino acids of equal length in water," Phys. Chem. Chem. Phys., 2006, vol. 8, pp. 333-339.
Slatkin, D.N. et al., "The use of heavy water in boron neutron capture therapy of brain tumours," Phys. Med. Biol., 1983, vol. 28, No. 12, pp. 1447-1451.
Tai, C-H. et al., "Automatic Microfluidic Platform for Cell Separation and Nucleus Collection," Biomed Microdevices, 2007, vol. 9, pp. 533-543.
Takahashi, K. et al., "Induction of Pluripotent Stem Cells from Mouse Embryonic and Adult Fibroblast Cultures by Defined Factors", Cell, Aug. 25, 2006, vol. 126, pp. 663-676.
Takahashi, K. et al., "Non-destructive on-chip cell sorting system with real-time microscopic image processing," Journal of Nanobiotechnology, Jun. 3, 2004, vol. 2, 8 pages.
Tan, Wei-Heong, et al., "A Lamination Micro Mixer for µ-Immunomagnetic Cell Sorter", JSME Int. J., Ser. C, 2005, vol. 48, No. 4, pp. 425-435 (1-29).
Tsenkova, R.N. et al., "Prion protein fate governed by metal binding," Biochemical and Biophysical Research communications, 2004, vol. 325, pp. 1005-1012.
Turkevich, J., "Colloidal Gold. Part 1. Historical and Preparative Aspects, Morphology and Structure," Gold Bull., 1985, vol. 18, No. 3, pp. 86-91.
Turkevich, J., et al., "A study of the nucleation and growth processes in the synthesis of colloidal gold," Discuss. Faraday Soc., 1951, vol. 11, pp. 55-75.
Voldman, J., "Electrical Forces for Microscale Cell Manipulation," Annual Review of Biomedical Engineering, 2006, vol. 8, pp. 425-454.
Wikipedia, "Infrared", Online Article, obtained online on Jun. 12, 2009 from url: http://en.wikipedia.org/wiki/Near-infrared, 12 pages.
Wikipedia, "Near Infrared Spectroscopy", Online Article, obtained online on Jun. 12, 2009 from url: http://en.wikipedia.org/wiki/Near_infrared_spectroscopy, 5 pages.
Wiltshire, M. et al., "A Novel Deep Red/Low Infrared Fluorescent Flow Cytometric Probe, DRAQ5NO, for the Discrimination of Intact Nucleated Cells in Apoptotic Cell Populations," Cytometry, Feb. 22, 2000, vol. 39, pp. 217-223.
Yamada, M. et al., "Microfuidic Particle Sorter Employing Flow Splitting and Recombining," Analytical Chemistry, vol. 78, No. 4, Feb. 15, 2006, pp. 1357-1362.
Yang, J. et al., "Dielectric Properties of Human Leukocyte Subpopulations Determined by Electrorotation as a Cell Separation Criterion," Biophysics Journal, Jun. 1999, vol. 76, pp. 3307-3314.
Yuyama, K. et al., "Nanoparticle preparation of quinacridone and Beta-carotene using near-infrared laser ablation of their crystals," Appl. Phys. A., 2010, vol. 101, pp. 591-596.
Zheng, S. et al., "Streamline-Based Microfluidic Devices for Erythrocytes and Leukocytes Separation," Journal of Microelectromechanical Systems, Aug. 2008, vol. 17, No. 4, pp. 1029-1038.
U.S. Final Office Action for U.S. Appl. No. 12/628,721, mailed on Oct. 11, 2013, 16 pp.
"Infrared spectrometer measures D2O in H2O," accessed at http://web.archive.org/web/20080401090647/http://www.laboratorytalk.com/news/wie/wie110.html, pp. 1-3, Dated Jul. 8, 2005.
Choi, S.Y., et al., "Feasibility of Fourier Transform (FT) Infrared spectroscopy for monitoring heavy water concentration in pressurized heavy water reactor," Vibrational Spectroscopy, vol. 31, pp. 251-256 (2003).
Non-Final Office Action in U.S. Appl. No. 12/628,721 dtd Feb. 11, 2015 (24 pages).
Shirota, H., et al., "Deuterium Isotope Effect on Volume Phase Transition of Polymer Gel: Temperature Dependence," The Journal of Physical Chemistry B, vol. 103, No. 47, pp. 10400-10408 (1999).

* cited by examiner

A
B

NIR FLUORESCENCE OF HEAVY WATER

CROSS-REFERENCE TO RELATED APPLICATIONS

This application is a U.S. national stage application under 35 U.S.C. §371 of PCT application No. PCT/IB2011/000733, filed on Apr. 5, 2011, which in turn claims the benefit of India Patent Application 196/KOL/2011, filed on Feb. 15, 2011, the disclosures of which are incorporated herein by reference in their entirety for any and all purposes.

RELATED APPLICATIONS

This application is related to U.S. Utility application Ser. No. 12/628,721, filed on Dec. 1, 2009, and to PCT/IB2010/001954, filed on Aug. 6, 2010, which claims the benefit of India Patent Application 467/KOL/2010, filed on Apr. 26, 2010. Each of these related applications are incorporated by reference in their entirety for any and all purposes.

TECHNOLOGY

The present technology is related in general to spectroscopic analysis of water and heavy water and of materials containing water and heavy water.

BACKGROUND

Structural changes of water and water distribution in a sample are difficult to monitor. One manner in which they may be studied is through isotopic substitution. For example, $^3H$ (tritium) may be used to label water and trace it via radioactive decay. However, because it is radioactive, wide application of such a technique is necessarily limited. The other isotope $^2H$ (deuterium) is found in nature as $D_2O$ (or heavy water) which was traditionally confined to the domain of nuclear physics and chemistry, for example as a reference in $^1H$ NMR.

One difficulty in conducting $D_2O$-based experiments is that there is no existing direct method of detecting $D_2O$. One can however indirectly see its effect, for example, how differently it reacts with a substrate as compared to water. Thus, methods are needed to detect and monitor $D_2O$ both qualitatively and quantitatively.

SUMMARY

The following summary is illustrative only and is not intended to be in any way limiting. In addition to the illustrative aspects, embodiments, and features described above, further aspects, embodiments, and features will become apparent by reference to the following drawings and the detailed description.

In one aspect, a method is provided for obtaining the near infrared fluorescence (NIRF) spectrum of a sample including a nanoparticle or cell or microparticle in enriched or pure $D_2O$. As used herein, obtaining refers to recordation of the spectrum in either physical or electronic form. In some embodiments, the spectrum is obtained at a wavelength of the NIRF spectrum from about 900 nm to about 1000 nm when the $H_2O$ and $D_2O$ samples are excited at the a given excitation wavelength in the range about 620 to about 640 nm.

In another aspect, a method is provided for detecting a biomolecular nanoparticle or a biological cell in a $H_2O$ and a $D_2O$ sample by detecting a difference in the near infra-red emission (NIRF) spectrum of the $H_2O$ and $D_2O$ samples containing the biomolecular nanoparticle or biological cell. In some embodiments, the difference is detected at a wavelength of the NIRF spectrum from about 850 nm to about 960 nm when the $H_2O$ and $D_2O$ samples are excited at the a given excitation wavelength in the range about 620 to about 640 nm. In $H_2O$, the spectral maxima near about 890-900 nm is conspicuous and in the $D_2O$ spectrum an additional peak near 960 nm emerges. There is small isotopic wavelength maxima shift in either of the ranges (i.e., near 900 nm and 960 nm). The spectral pattern for water and heavy water changes in the presence of nanoscale objects (nanoparticles). While the position of the maxima around 900 nm and 960 nm changes insignificantly, the spectral intensity around theses peaks changes depending on the embodiment (e.g. DNA, nanoparticle, or cancer cell).

In other embodiments, the difference NIRF measures a relative contribution of water in a cellular interior. As used herein, relative contribution refers to the NIRF emission contribution that is attributed to formation of the water clusters, taking into consideration the hydrophobic effect which is based on the ordering of water molecules, leading to self assembly of various kinds; e.g., membranes of cells, intracellular compartments.

In another aspect, a method is provided including detecting nanoparticles or microparticles in a $H_2O$ and a $D_2O$ sample by detecting a difference in the near infra-red fluorescence (NIRF) spectrum of the $H_2O$ and $D_2O$ samples containing the nanoparticles or microparticles. In some embodiments, the method also includes monitoring a change in intensity or signal to noise of the difference NIRF spectrum as a function of temperature.

In another aspect, a method is provided including detecting a nanoparticle or cell in a $H_2O$ sample; detecting the nanoparticle or cell in a $D_2O$ sample; determining a difference in the near infra-red fluorescence (NIRF) spectrum of the $H_2O$ and $D_2O$ samples containing the nanoparticle or cell; and cataloging the difference to build a library of difference NIRF spectra. In some embodiments, the difference is detected at a wavelength of the NIRF spectrum from 850 nm to 960 nm when the $H_2O$ and $D_2O$ samples are excited at the same excitation wavelength. In another embodiment, the excitation wavelength is 627 nm. In other embodiments, the difference is a shift of a spectral maximum in the NIRF of the $D_2O$ spectrum as compared to the $H_2O$ spectrum. In other embodiments, the difference is the presence of one or more spectral maxima in the $D_2O$ spectrum that are absent in the $H_2O$ spectrum. In yet other embodiments, the detecting, determining, and cataloging are repeated for more than two nanoparticles or cells of different origin. In some embodiments, the nanoparticle or cell is of biological origin.

In some embodiments, the method also includes obtaining a difference spectrum of a nanoparticle or cell of unknown identity or origin and comparing it to the library of difference NIRF spectra to identify the nanoparticle or cell of unknown identity or origin.

In some embodiments, the method also includes obtaining a difference NIRF spectrum of a nanoparticle or cell of unknown size and comparing it to the library of difference NIRF spectra to identify the size of the nanoparticle or cell.

BRIEF DESCRIPTION OF THE DRAWINGS

FIGS. 5A-D are related to nanoparticle sizes of 32 nm, 43 nm, 58 nm, and 70 nm, respectively.

DETAILED DESCRIPTION

Figure 1:
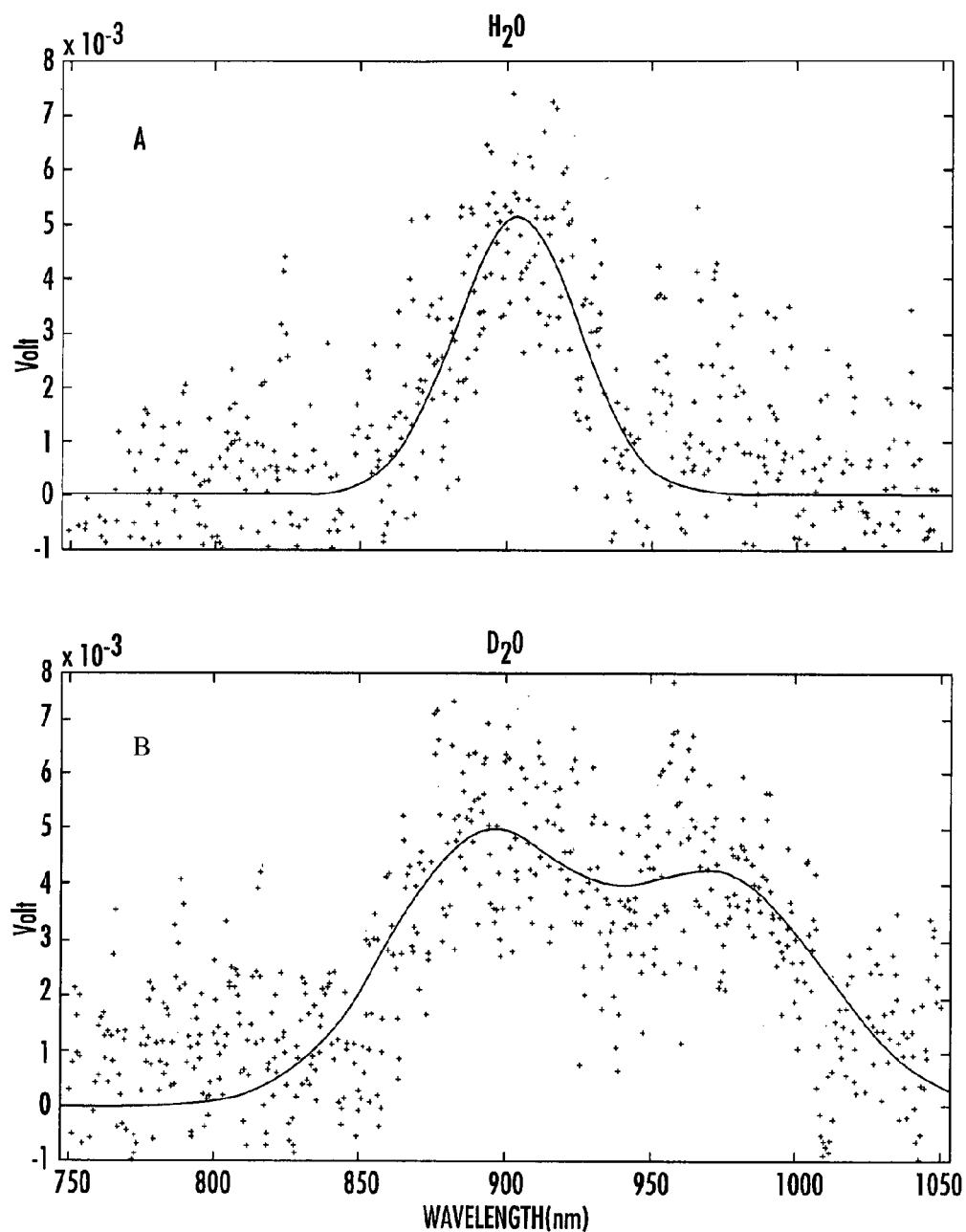
FIGS. 1A and 1B are graphs of the Gaussian fitted emission spectra of water (A) and $D_2O$ (B) in the NIR region upon excitation at 640 nm, according to an illustrative embodiment.

In the following detailed description, reference may be made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Water is implicitly associated with every precursor that led to chemical and biological evolution. Networks of H-bonds in water are in constant flux, forming and breaking in response to solutes. The networks form clathrate or cage-like structures, and coherent nano clusters. Each water monomer (i.e. isolated $H_2O$) has dipolar strength of approximately 1.86 Debye, which increases several fold upon ionization, or cluster formation. The NIRF emission reflects the hydrogen bond network signature, and with $D_2O$ containing a higher density of hydrogen bonding as compared to water, altered emission pattern has now been observed in $D_2O$ samples. Colloidal nanoparticles, or biological cells each having a characteristic interfacial water signature also provide a characteristic NIRF intensity pattern.

Near infrared fluorescence (NIRF) spectroscopy may be used for the direct detection of $D_2O$. As used herein, the term 'direct detection' means measuring a spectroscopic response of $D_2O$, that is directly attributable to the $D_2O$. The direct evidence can be measured with or without the presence of $H_2O$. In comparison, the term 'indirect detection' is measuring a response from $D_2O$ that can only be obtained by comparing how differently it reacts with a substrate as compared with water. Hydrogen bonds are known to play a role in the behavior of water, yet, accurately detecting the making and breaking of hydrogen bonds in water is difficult. However, $D_2O$ will freely hydrogen/deuterium exchange with water, and this exchange may be exploited to probe the localized structure and ordering of water using NIRF.

It has been observed that a Stokes shift in the fluorescence of a water sample, a $D_2O$ sample, or mixed sample, occurs in the NIR region of the spectrum, and is indicative of the presence of water, $D_2O$, or HDO. As used herein, the Stokes shift is as commonly understood in the art. It is described as the difference (in wavelength or frequency units) between positions of the band maxima of the absorption and emission spectra of the same electronic transition. For $H_2O$ and $D_2O$, the fluorescence spectrum in the NIR exhibits an absorption maximum from 630 nm to 650 nm and an emission maxima from 850 nm to 915 nm and from 950 nm to 1000 nm. In some embodiments, the absorption maximum is observed from 620 nm to 640 nm. In yet other embodiments, the absorption maximum is 640 nm. In yet other embodiments, the absorption maxima is 627 nm. In some embodiments, the emission maximum is observed from 900 nm to 905 nm and from 955 nm to 965 nm. In yet other embodiments, the emission maxima is observed at a wavelength centered on 905 nm and on 960 nm. Related application U.S. patent application Ser. No. 12/628,721 discloses that a Stokes shift of 200-300 nm occurs when $H_2O$ is excited at 647 nm in the NIR region.

While both water and $D_2O$ exhibit the Stokes shift in emission at the same absorption, $D_2O$ exhibits an altered emission pattern over that of water. For example, the excitation and fluorescence signals for water and $D_2O$ are shown in FIGS. 1A and 1B, respectively. As shown in the FIGS. 1A and 1B, the signal for $D_2O$ shows an approximate order of magnitude increase in intensity (Y axis, i.e. Volt), with a significant improvement in the signal-to-noise ratio. Without being bound by theory, it is believed that the NIRF is a reflection of the fluctuating three-dimensional network of hydrogen bonds in liquid water and $D_2O$ clusters, rather than a result of individual molecules of water or $D_2O$. It is believed that such a marked difference in intensity can only arise due to difference at the 3D cluster level rather than at the level of single bond stretching. It is known that the number of hydrogen bonds per water molecule in $H_2O$ is less than that in $D_2O$ (3.62 vs. 3.76). The additional factor causing such higher NIRF intensity may be due to the stronger hydrogen-like bonds present in $D_2O$ (i.e. because pure $D_2O$ does not have hydrogen, the bonds are not hydrogen bonds, but instead the deuterium forms a bond similar to that for hydrogen).

Figure 2:
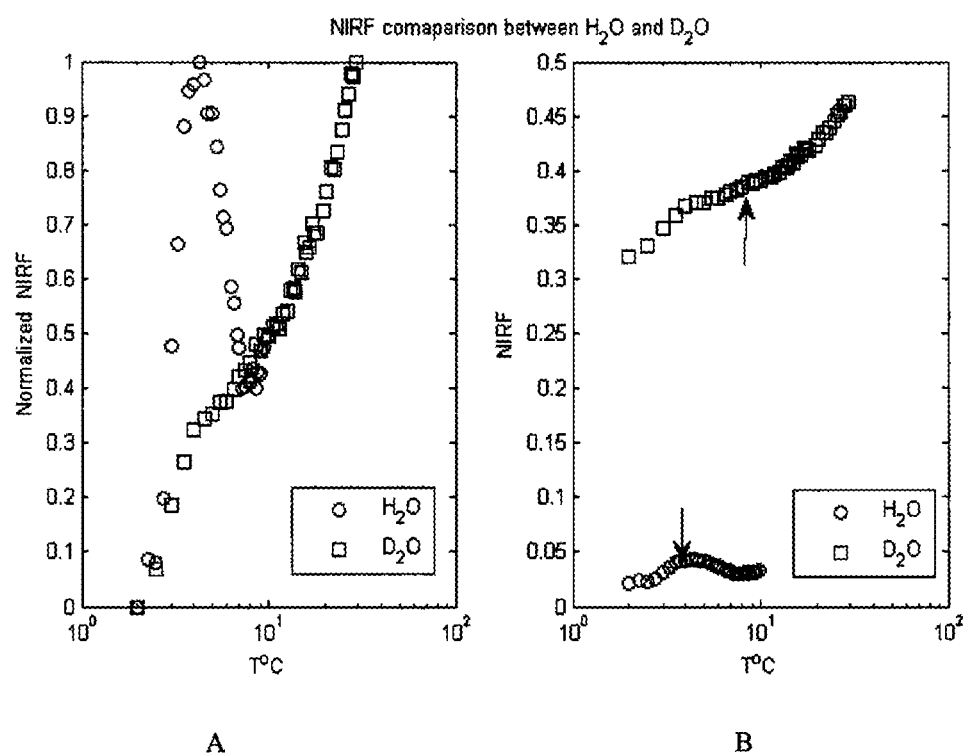
FIGS. 2A and 2B are graphs of the NIRF for $D_2O$ and $H_2O$ for both normalized NIRF (2A) and absolute NIRF (2B) as a function of temperature.
Figure 3:
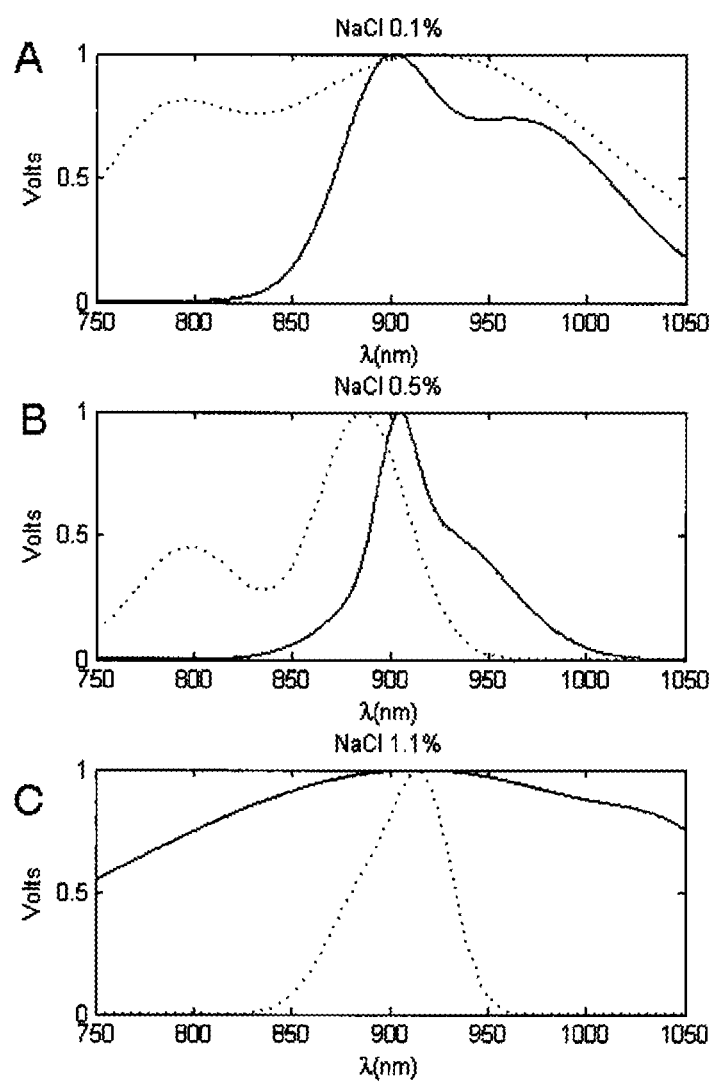
FIGS. 3A-F are graphs of the NIRF intensity variation with respect to variation of NaCl concentration, according to an illustrative embodiment. The dashed lines are $D_2O$-saline and the solid lines are $H_2O$-saline.
Figure 3:
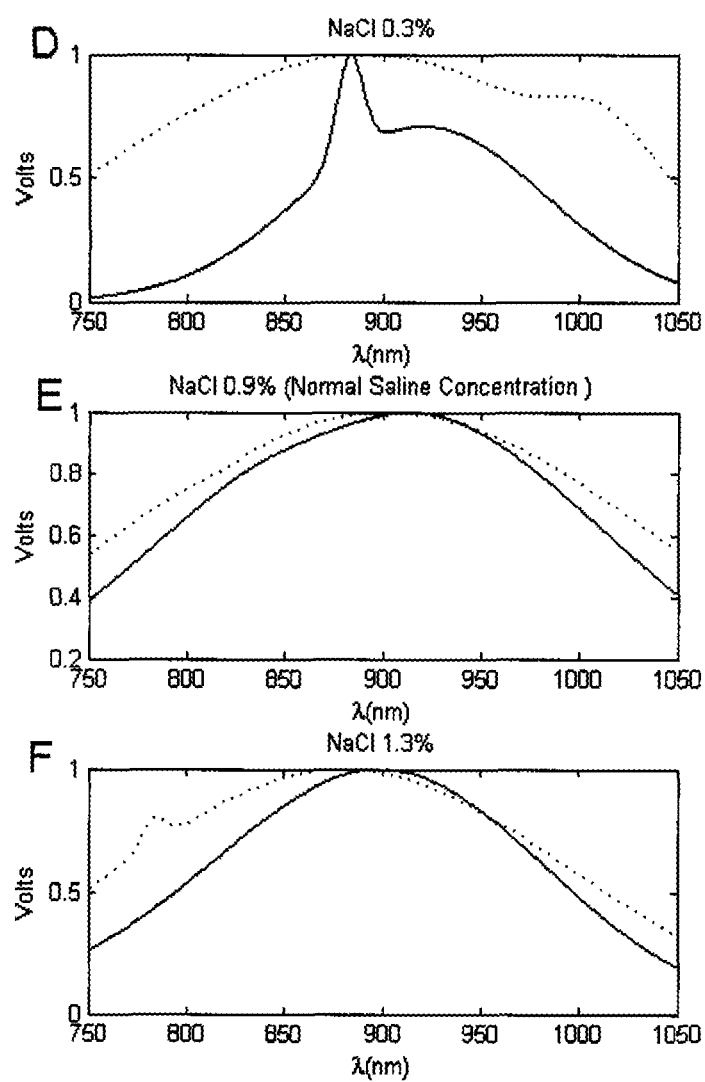
Figure 4:
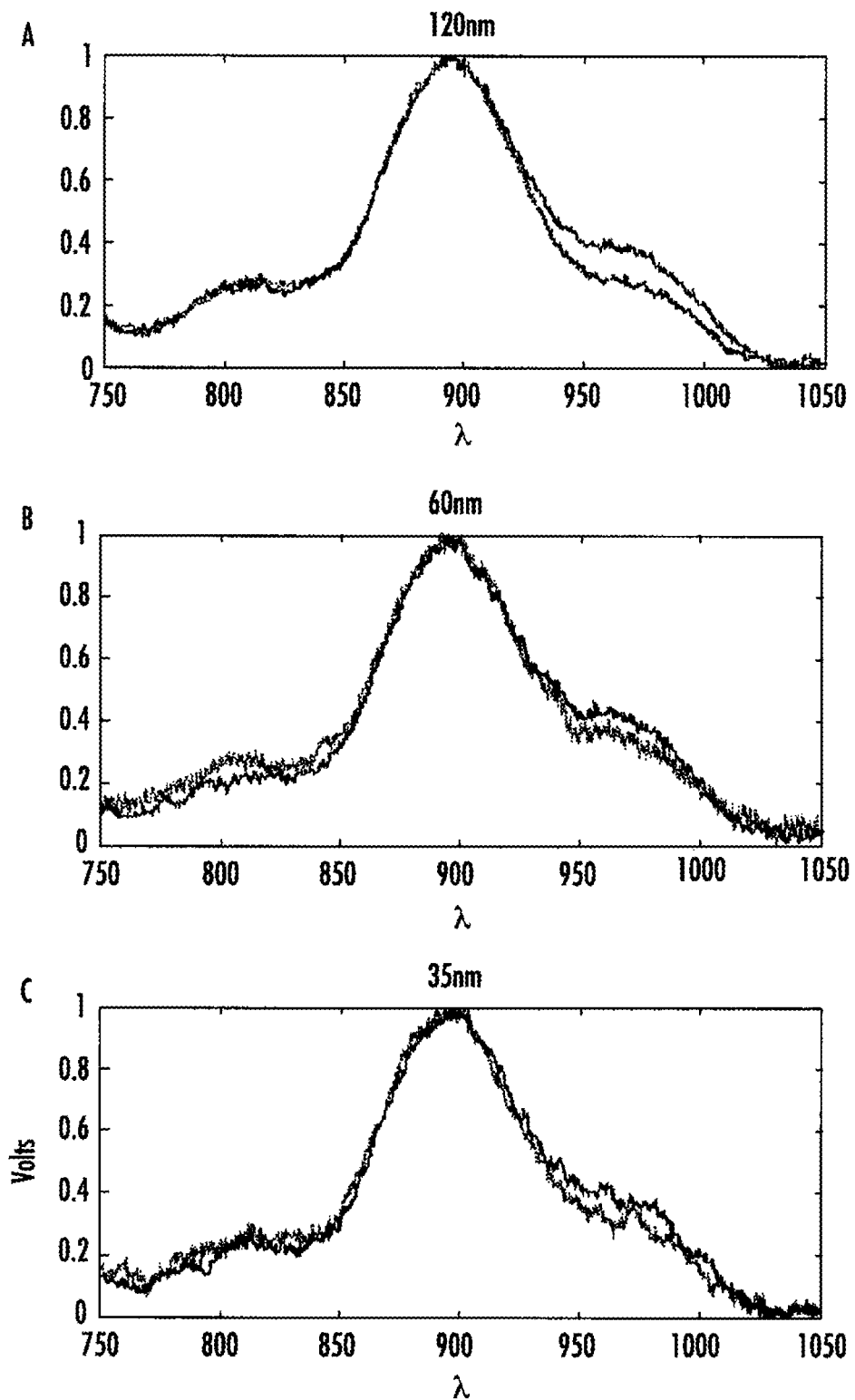
FIGS. 4A-E are normalized graphs showing the difference between NIRF spectra in $H_2O$ and $D_2O$ for gold nanoparticles, according to an illustrative embodiment.
Figure 4:
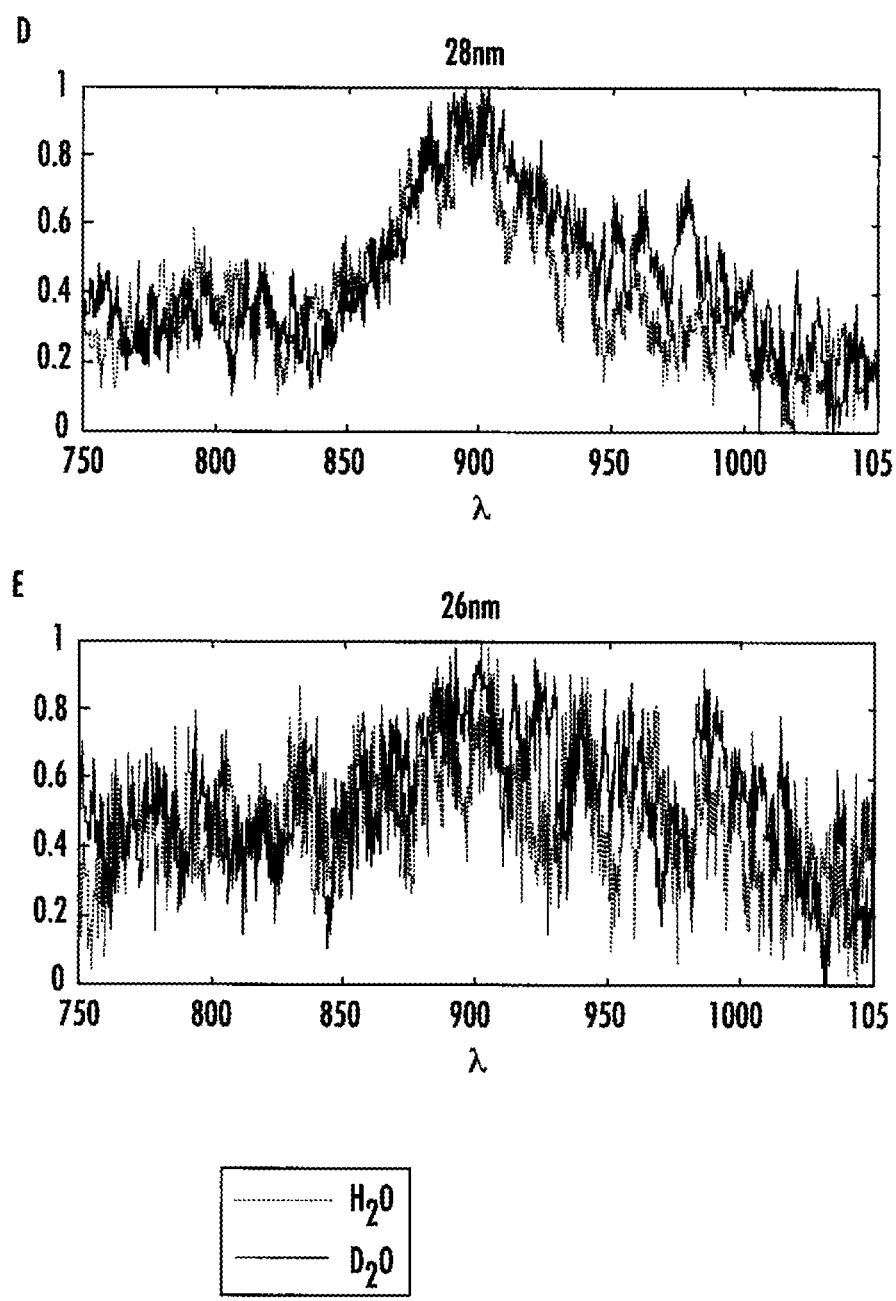
Figure 5:
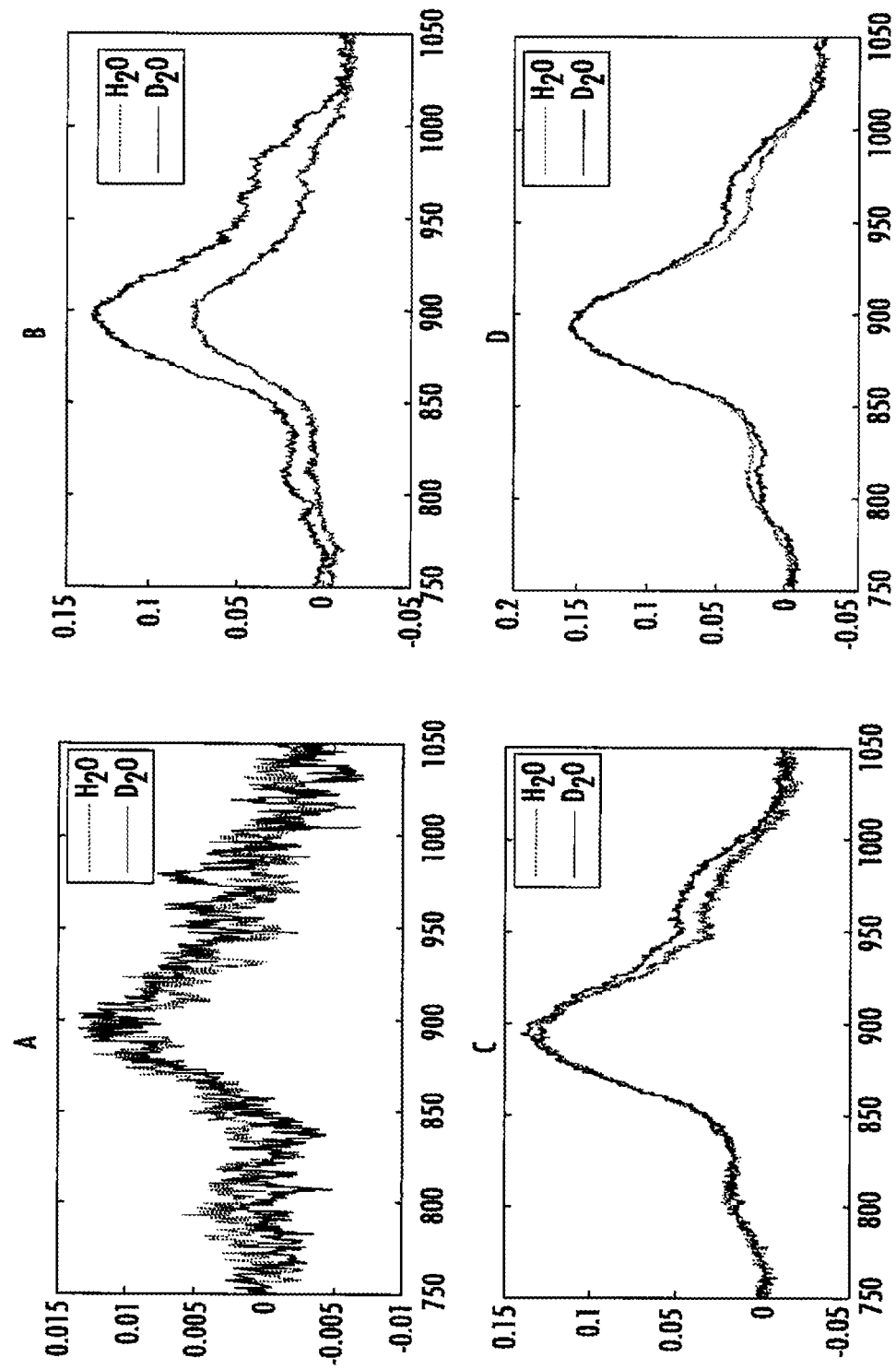
FIGS. 5A-D are normalized graphs showing enhancement of NIR emission intensity by nanoparticles as a function of particle size.

It has also been observed that temperature variation affects the NIRF intensity. FIGS. 2A and 2B illustrate intensity changes as a function of temperature, indicative of water and $D_2O$. FIG. 2A illustrates the variation of normalized NIRF intensity (Intensity−min(Intensity))/(Max(Intensity)−Min (Intensity)) for the respective isotopes. FIG. 2B illustrates the NIRF intensity under identical excitation, and that there is approximately an order of magnitude enhancement of intensity of $D_2O$ relative to $H_2O$. The arrow in the respective plots (4° C. in the case of water and about 11° C. in the case of $D_2O$) indicates the regimes of maximal density of the isotopes. In generating the data for FIG. 2, the excitation and emission were taken at 647 nm and 905 nm, respectively. The temperature profile is much flatter for $D_2O$ than for water, with a mild break appearing at the maximal density region. Without being bound by theory, it is believed that stronger hydrogen bonding in $D_2O$ is the cause of such monotonic emission change. Thus, in some embodiments, the NIRF intensity is optimized at low temperatures for water and $D_2O$ samples. In some embodiments, the NIRF intensity is optimized for both water and $D_2O$ from 0° C. to 10° C. In other embodiments, the NIRF intensity is optimized for both water and $D_2O$ from 2° C. to 6° C. In yet other embodiments, the NIRF intensity is optimized for both water and $D_2O$ at 4° C.

It is observed that, when salt is added to the water, and the salinity of the solution is varied, the maximal intensity for the NIRF also varies. This is illustrated by FIGS. 3A-3F which show the variations of NIRF spectra in both $D_2O$ and $H_2O$ at varying salt concentrations. It is, however, striking to note that the spectra are most well-matched at the physiological saline concentration (0.9%). In view of the change in spectra at different concentrations, in one embodiment, a method includes determining the salt concentration of a saline solution (with or without $D_2O$) using NIRF and comparing it to standard curves.

The NIR emission intensity is also observed to vary in the presence of microscale and nanoscale colloidal objects such as but not limited to biomolecules like DNA, nanoparticles, nanoparticles (capped or conjugated with small molecules or biomolecules), or microparticles (particles having one or more micron scale dimensions) such as, but not limited to, cells.

Introduction of nanoscale colloidal objects to $H_2O$ or $D_2O$ raises the NIR emission intensity by several orders of magnitude. This increase is a function of the hydrodynamic size of the nano(micro)particle. The hydrodynamic size of the nano- or micro-particles may be from 10 nm to 100 μm. Further, the nano- or micro-particles may be partially or completely coated. As used herein, coating of a nanoparticle refers to the presence of a material conjugated to the surface of a nano (micro)particle either by covalent or noncovalent interactions (e.g. hydrogen bonding or van der waals forces). In illustrative embodiments, particles include, but are not limited to, 20-150 nm gold nanoparticles (GNP), 30-150 nm GNP that have been coated with arginine, and 60 nm latex particles. As discussed in more detail below, the Stokes signal can be amplified in the presence of $D_2O$, e.g., note the emission intensity difference between that of $D_2O$ and $H_2O$. This difference renders $D_2O$ suitable for use as an NIRF label. For example, gold nanoparticles of various sizes shows the difference between $H_2O$ and $D_2O$ spectra of Au nanoparticles as the size changes from 26 to 120 nm (see FIGS. 4A-E). As illustrated in FIGS. 5A-D, as the nanoparticle size increases (32 nm (FIG. 5A), 43 nm (FIG. 5B), 58 nm (FIG. 5C), and 70 nm (FIG. 5D), respectively), the NIR emission intensity increases along with the signal-to-noise ratio, with $D_2O$ showing predominantly higher intensity at 960 nm. Latex nano-sphere and gold nanoparticles both having an average hydrodynamic diameter of 60 nm, showed different NIR emission intensity profiles with respect to variation of temperature. The data suggest that mild modification of the colloidal nanosurface can lead to a change in the emission properties of hydrogen-bonded networks. This implies that surface conjugation affects the emission properties of the interfacial water clusters depending on the nature of surface conjugation. Thus, in some embodiments, calibration curves may be prepared of intensity of NIR emission as a function of particle size for a known particle concentration at a known temperature. Based upon the calibration curves, the size of the particles, or range of sizes of the particles, in the water or $D_2O$ may then be determined.

Accordingly, in one aspect, a method is provided including detecting particles or cells in a $D_2O$ sample by obtaining a near infra-red fluorescence (NIRF) spectrum of the $D_2O$ sample containing the particles or cells. In some embodiments, the particles are nanoparticles or microparticles. In some embodiments, the method includes monitoring a change in intensity or signal to noise ratio of the NIRF spectrum as a function of temperature. In some embodiments, the NIRF spectrum of the particles or cells is also obtained in $H_2O$ and a difference in the near infra-red fluorescence (NIRF) spectrum of the $H_2O$ and $D_2O$ samples containing the particles or cells is determined.

In some embodiments, the methods provided include detecting nanoparticles or cells or microparticles in a $H_2O$ sample and in a $D_2O$ sample by observing a difference in the near infra-red fluorescence (NIRF) spectrum of the $H_2O$ and $D_2O$ samples containing the biomolecular nanoparticle or biological cell. In some embodiments, the difference is detected at a wavelength of the NIRF spectrum from 850 nm to 960 nm when the $H_2O$ and $D_2O$ samples are excited at the same excitation wavelength. In some embodiments, the excitation wavelength is 627 nm.

Figure 6:
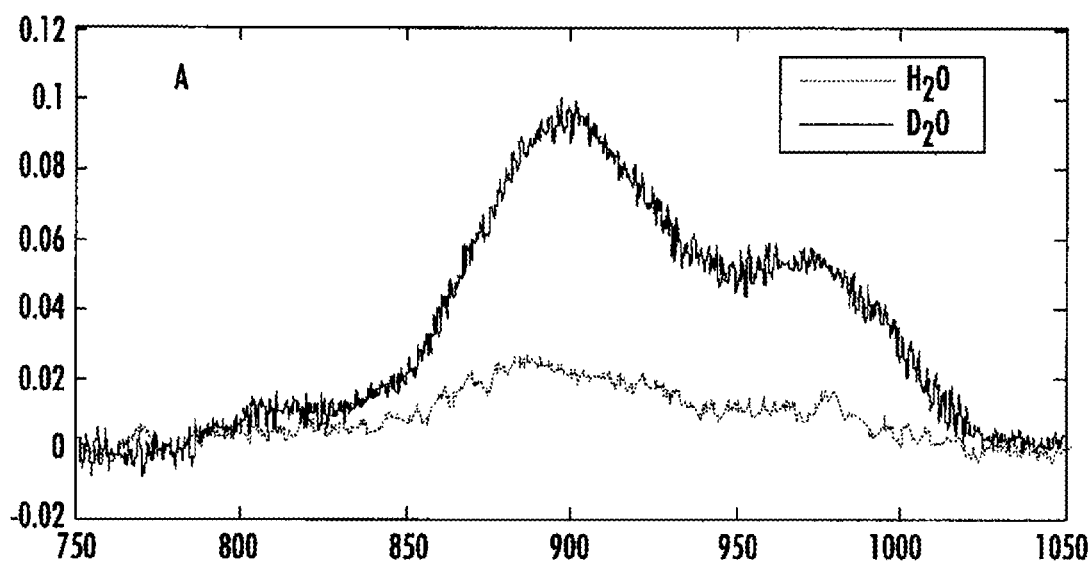
FIGS. 6A and 6B are graphs of the altered fluorescence pattern (A: upper panel) and the isotopic shift (B: indicated by the arrow in the normalized emission spectra) observed in case of $H_2O$ and $D_2O$ in calf thymus DNA (0.5 mg/ml).
Figure 6:
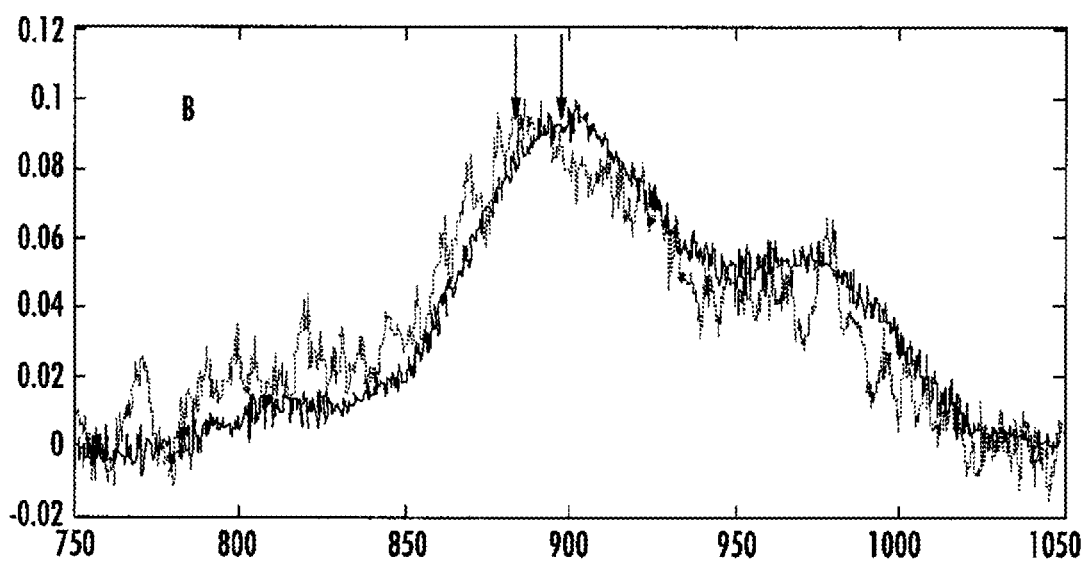
Figure 7:
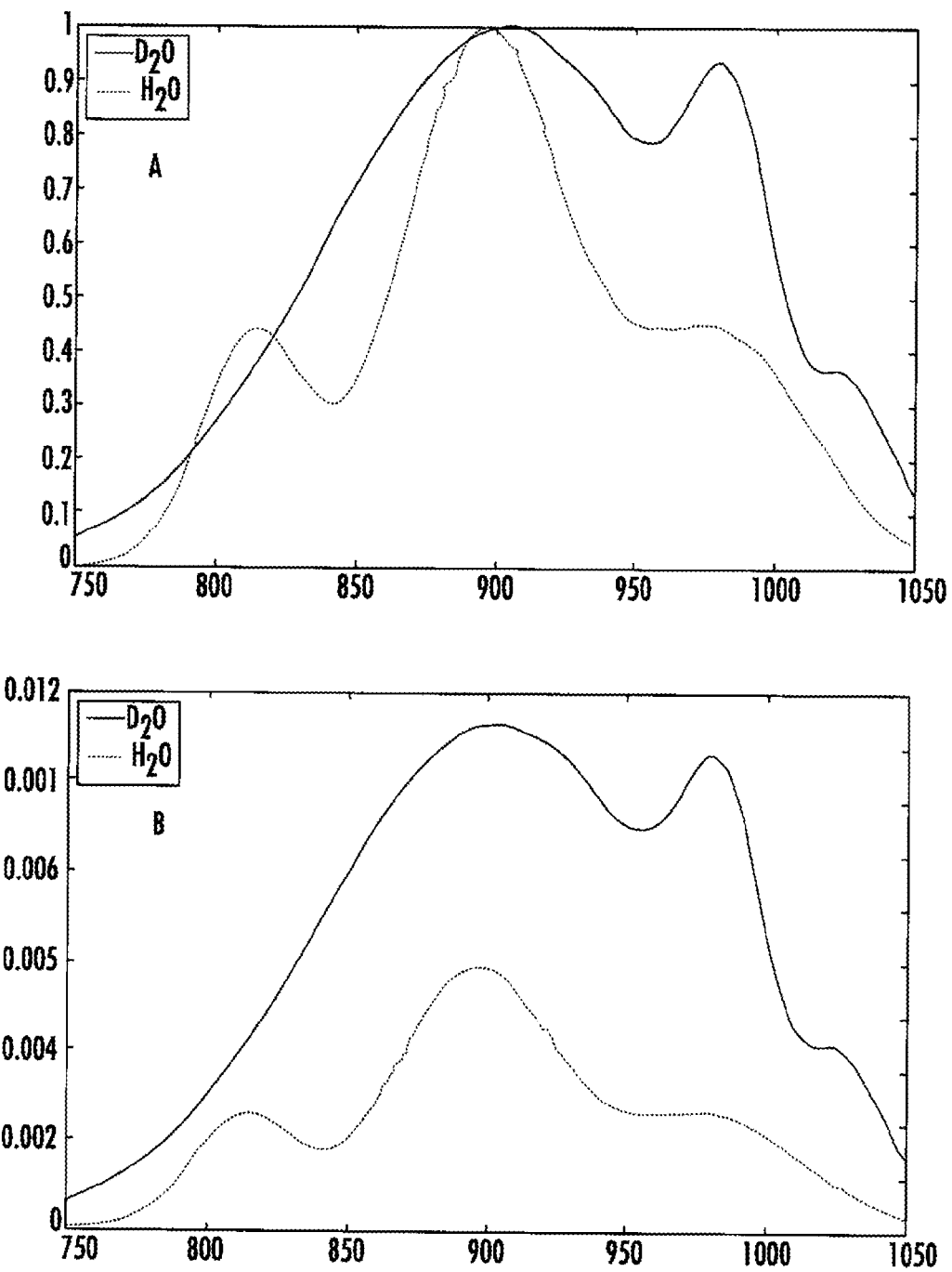
FIGS. 7A and 7B are graphs of the different spectral maxima in the normalized data (A: upper panel) and non-normalized spectra (B: lower panel) in case of $H_2O$ and $D_2O$ samples in salmon sperm DNA (0.5 mg/ml).
Figure 8:
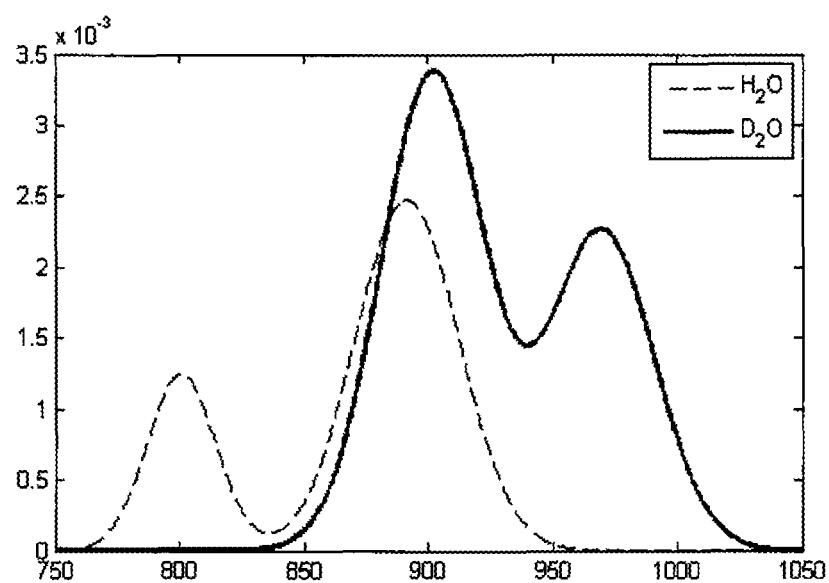
FIG. 8 represents the $H_2O$ and $D_2O$ NIRF spectra respectively of RPMI8226 cancer cells (Human Myeloma cell line), where the ordinate represents emission intensity in volts and abscissa represents the wavelength in nm.

In some embodiments, the observing a difference in the NIRF spectrum includes observing a shift of between 5 nm and 20 nm of a spectral maxima in the NIRF in the $D_2O$ spectrum as compared to the $H_2O$ spectrum. In other embodiments, the observing a difference in the NIRF spectrum includes observing the presence of one or more spectral maxima in the $D_2O$ spectrum that are absent in the $H_2O$ spectrum, but where a central maxima common to both the $H_2O$ and $D_2O$ spectra is unchanged. As illustrative examples of such observations. FIG. 6 shows that a shift in the NIRF spectrum for $D_2O$ in the presence of calf thymus DNA is observed in comparison to the NIRF spectrum for the calf thymus DNA in water, and FIG. 7 shows the different spectral maxima in $H_2O$ and $D_2O$ samples for salmon sperm DNA. FIG. 8 is a graph of the $H_2O$ and $D_2O$ NIRF spectrum respectively with RPMI8226 cancer cells (Human Myeloma cell line). The two spectra show variations in emission spectra and intensity.

In another embodiment, the method is configured to evaluate the relative contribution of bound water and free water in for example cellular functions, as biological cellular processes occur in water, or in green chemical processes, which are conducted in aqueous solution.

Bound water generally refers to the water at an interface of two materials. For example, between two phases such as a fluid phase and a solid or semi-ordered phase. In such materials, water is bound to, adsorbed to, or otherwise associated with the solid or semi-ordered phase. Bound water at the interface between tissue fluid and a cellular organelle such as a biomembrane is bound to, or associated with, macromolecules of the biomembrane. Experiments have shown that interfacial water provides a higher NIRF intensity than free water. In terms of imaging, a differential typically exists between water at the interface (i.e. the bound water) and the water in the surroundings (i.e. the free water, or bulk water) arising from different properties of bound water and free water such as a difference in NIRF intensity. For example, for a cell surrounded by a medium, the differential contrast is proportional to how much water is bound to the cell as compared to how much water is in the surrounding medium. As disclosed herein, the interface intensity can be studied with higher efficiency using $D_2O$, rather than using pure $H_2O$, because the NIRF intensity of $D_2O$ is approximately an order of magnitude greater than the NIRF intensity of $H_2O$.

In another aspect, a method is provided including detecting a nanoparticle or cell in a $D_2O$ sample using NIRF, and building a library of such spectra for the determination of unknown materials. The cataloging of the spectra can provide valuable information as described above in characterizing unknown materials, providing information about particle sizes, and as a complementary tool in noninvasive imaging where NIRF fluorescence of cell may provide information regarding the aqueous environment of the system.

In another aspect, a method is provided including detecting a nanoparticle or cell in a $H_2O$ sample; detecting the nanoparticle or cell in a $D_2O$ sample; determining a difference in the near infra-red fluorescence (NIRF) spectrum of the $H_2O$ and $D_2O$ samples containing the nanoparticle or cell; and cataloging the difference to build a library of difference NIRF spectra.

To determine the NIRF difference spectra described above, the difference may be detected at a wavelength of the NIRF spectrum from 850 nm to 960 nm when the $H_2O$ and $D_2O$ samples are excited at the same excitation wavelength. For example, when the $H_2O$ and $D_2O$ samples are both excited at 627 nm. The difference may manifest itself in various forms. For example, the difference may be a shift of a spectral maximum in the NIRF of the $D_2O$ spectrum as compared to the $H_2O$ spectrum. Or, the difference may be the presence of one or more spectral maxima in the $D_2O$ spectrum that are absent in the $H_2O$ spectrum. As an illustration, the $H_2O$ spectrum may display 2 peaks, and the $D_2O$ spectrum, while similarly exhibiting the same two peaks may exhibit a third or fourth peak as well. The detecting, determining, and cataloging are then repeated for a multitude of a nanoparticles, or of cells of different origin, such that a broad library may be built for the identification of unknown materials. The nanoparticles may be of non-biological or biological origin. For example, the nanoparticles may be of mineral, polymer, micellular, or biological origin.

In some embodiments, the method also includes obtaining a difference spectrum of a nanoparticle or cell of unknown identity or origin and comparing it to the library of difference NIRF spectra to identify the nanoparticle or cell of unknown identity or origin. In some embodiments, the method also includes obtaining a difference NIRF spectrum of a nanoparticle or cell of unknown size and comparing it to the library of difference NIRF spectra to identify the size of the nanoparticle or cell.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The present technology, thus generally described, will be understood more readily by reference to the following examples, which are provided by way of illustration and are not intended to be limiting of the present technology.

EXAMPLES

The present technology is further illustrated by the following examples, which should not be construed as limiting in any way. The following definitions are used herein.

To detect the NIRF, spectra were acquired using PTI fluorometer with NIR interface. The interface was equipped with a high intensity 75 watt Xenon light source, high sensitivity TE-cooled InGaAs detector, lock-in amplifier and chopper for noise suppression. The detector was also equipped with a monochromater having a 600 groove grating blazed at 1.2 microns. The data was acquired and stored through FeliX32 software (provided along with the instrument by PTI, USA). The software package included 32-bit fluorescence analysis. A 620 nm cut-off filter was used at the emission channel before the NIR detector to prevent unnecessary entry of stray light at the NIR region.

Synthesis of Nanoparticles. The gold nanoparticles were prepared by the standard method of Turkevich and Frens [Turkevich, J. et al. *Discuss. Faraday Soc.* 1951, 11, 55; Turkevich, *J. Gold Bull.* 1985, 18, 86; and Frens, G. *Nature (London): Phys. Sci.* 1973, 241, 20.] with some modifications. A continuously stirred aqueous solution of $HAuCl_4$ (2.5 µM, 25 mL) was brought to boiling, and freshly prepared trisodium citrate solution (38.8 mM) was added at varying concentrations, depending on the requirement of the particle size. The additional of the trisodium citrate resulted in a change in the color of the solution from pale yellow to deep red. When the color persisted, the temperature was allowed to return to ambient, and the colloidal solution was stirred for an additional 5 minutes. Where arginine conjugated nanoparticles were prepared, 2-10 µM L-arginine was added immediately prior to the addition of the trisodium citrate. The hydrodynamic size of the nanoparticles was determined using NanoZS (Malvern, UK).

Comparison of spectral behavior of nanoparticles microparticles or cells suspended in water and heavy water. NIRF studies were performed by using excitation range 630 nm (spectra remained almost identical with 10 nm variation). For experiments with heavy water, water was removed by centrifugation. The pellet containing the nanoparticles was then re-suspended in $D_2O$. Similar re-suspension methods were followed for comparison of the NIRF behavior of microparticles and/or cells.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting' of excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method comprising:
causing light to enter a first sample comprising a nanoparticle, microparticle, or cell from a source in a $H_2O$ sample;
detecting light exiting the first sample;
determining a first near infra-red fluorescence (NIRF) spectrum based on the detected light exiting the first sample;
causing light to enter a second sample from the source comprising a nanoparticle, microparticle, or cell in enriched or pure $D_2O$;
detecting light exiting the second sample;
determining a second NIRF spectrum based on the detected light exiting the second sample; and
determining a difference NIRF spectrum of the first NIRF spectrum and the second NIRF spectrum.

2. The method of claim 1, wherein the light exiting the first sample and the light exiting the second sample has a wavelength from about 850 nanometers (nm) to about 1000 nm.

3. The method of claim 2, wherein the light entering the first sample and the light entering the second sample has a wavelength from about 620 nm to about 640 nm.

4. The method of claim 1, further comprising cataloging the difference NIRF spectrum to build a library of difference NIRF spectra.

5. The method of claim 4, wherein the determining the difference NIRF spectrum and the cataloging the difference NIRF spectrum are repeated for more than two nanoparticles, microparticles, or cells of different origin.

6. The method of claim 4, further comprising obtaining a difference NIRF spectrum of a sample comprising a nanoparticle, microparticle, or cell of unknown identity or origin and comparing it to the library of difference NIRF spectra to identify the nanoparticle or cell of unknown identity or origin.

7. The method of claim 4, further comprising obtaining a difference NIRF spectrum of a sample comprising a nanoparticle or cell of unknown size and comparing it to the library of NIRF spectra to identify the size of the nanoparticle or cell.

8. The method of claim 1, wherein the nanoparticle, microparticle, or cell is of biological origin.

9. A method comprising:
detecting a nanoparticle, microparticle, or cell from a source in a $H_2O$ sample;
detecting a nanoparticle, microparticle, or cell from the source in a $D_2O$ sample;
determining a difference in the near infra-red fluorescence (NIRF) spectrum of the $H_2O$ and $D_2O$ samples containing the nanoparticle, microparticle, or cell; and
cataloging the difference to build a library of difference NIRF spectra.

10. The method of claim 9, wherein the difference is detected at a wavelength of the NIRF spectrum from about 850 nm to about 1000 nm when the $H_2O$ and $D_2O$ samples are excited at the same excitation wavelength.

11. The method of claim 9, wherein the excitation wavelength is about 620-640 nm.

12. The method of claim 9, wherein the difference is a shift of a spectral maxima in the NIRF of the $D_2O$ spectrum as compared to the $H_2O$ spectrum.

13. The method of claim 9, wherein the difference is the presence of one or more spectral maxima in the $D_2O$ spectrum that are absent in the $H_2O$ spectrum.

14. The method of claim 9, wherein the detecting, determining, and cataloging are repeated for more than two nanoparticles, microparticles, or cells of different origin.

15. The method of claim 9, further comprising obtaining a difference spectrum of a nanoparticle, microparticle, or cell of unknown identity or origin and comparing it to the library of difference NIRF spectra to identify the nanoparticle or cell of unknown identity or origin.

16. The method of claim 9, further comprising obtaining a difference NIRF spectrum of a nanoparticle, microparticle, or cell of unknown size and comparing it to the library of difference NIRF spectra to identify the size of the nanoparticle or cell.

17. The method of claim 9, wherein the nanoparticle, microparticle, or cell is of biological origin.

18. A method comprising:
obtaining a first sample and second sample from a singular source, the source comprising a nanoparticle, microparticle, or cell;
exposing the first sample in a $H_2O$ environment to an excitation source having a wavelength from 620 nm to 640 nm;
obtaining a first near infra-red fluorescence (NIRF) spectrum of the first sample at a wavelength from 850 nm to 1000 nm;
exposing the second sample in a pure or enriched $D_2O$ environment to the excitation source having a wavelength from 620 nm to 640 nm;
obtaining a second near infra-red fluorescence (NIRF) spectrum at a wavelength from 850 nm to 1000 nm; and determining a difference NIRF spectrum between the first spectrum and the second spectrum.

19. The method of claim 18, wherein the difference NIRF spectrum exhibits a shift of a spectral maxima in the NIRF of the second spectrum as compared to the first spectrum.

20. The method of claim 18, wherein the difference NIRF spectrum exhibits one or more spectral maxima in the second spectrum that are absent in the first spectrum.

\* \* \* \* \*